(12) United States Patent
Holt et al.

(10) Patent No.: US 9,668,889 B2
(45) Date of Patent: Jun. 6, 2017

(54) PERCUTANEOUS OSSEOINTEGRATED PROSTHETIC IMPLANT SYSTEM

(75) Inventors: Brian Mueller Holt, Topanga, CA (US); Kent N. Bachus, Salt Lake City, UT (US); Sujee Jeyapalina, Salt Lake City, UT (US); James Peter Beck, Salt Lake City, UT (US); Roy Bloebaum, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 33 days.

(21) Appl. No.: 14/123,719

(22) PCT Filed: Jun. 6, 2012

(86) PCT No.: PCT/US2012/041112
§ 371 (c)(1),
(2), (4) Date: Feb. 10, 2014

(87) PCT Pub. No.: WO2013/048589
PCT Pub. Date: Apr. 4, 2013

(65) Prior Publication Data
US 2014/0156022 A1    Jun. 5, 2014

Related U.S. Application Data

(60) Provisional application No. 61/493,914, filed on Jun. 6, 2011, provisional application No. 61/594,815, filed (Continued)

(51) Int. Cl.
*A61F 2/28* (2006.01)
*A61F 2/78* (2006.01)
(Continued)

(52) U.S. Cl.
CPC .............. *A61F 2/78* (2013.01); *A61F 2/2814* (2013.01); *A61C 2008/0046* (2013.01);
(Continued)

(58) Field of Classification Search
CPC ............ A61F 2/2814; A61F 2002/7887; A61F 2002/30013; A61F 2002/30029;
(Continued)

(56) References Cited

U.S. PATENT DOCUMENTS

| | | |
|---|---|---|
| 4,158,895 A | 6/1979 | Reswick et al. |
| 4,938,769 A | 7/1990 | Shaw |

(Continued)

FOREIGN PATENT DOCUMENTS

| | | | | |
|---|---|---|---|---|
| DE | 199 31 882 C1 | * | 5/2001 | ............... A61F 2/30 |
| DE | 10 2009 027 255 A1 | * | 8/2010 | ............... A61F 2/28 |
| WO | WO 2009/105535 A1 | | 8/2009 | |

OTHER PUBLICATIONS

International Search Report and Written Opinion of International Searching Authority for Corresponding PCT Application, PCT/US2012/041112; mailing date Mar. 13, 2013.

(Continued)

*Primary Examiner* — David H Willse
(74) *Attorney, Agent, or Firm* — EIP US LLP

(57) ABSTRACT

An implant system for securing a prosthesis to a selected bone of a subject including a stem and an abutment. The stem includes a porous region that promotes osseointegration of the selected bone following implantation of the stem. The abutment is secured to the stem and is configured for secure attachment to the prosthesis. The stem and the abutment include ultra-low friction and/or highly polished surfaces at select locations that inhibit bio-adhesion.

11 Claims, 7 Drawing Sheets

Related U.S. Application Data on Feb. 3, 2012, provisional application No. 61/622,783, filed on Apr. 11, 2012.

(51) Int. Cl.
- *A61F 2/30* (2006.01)
- *A61C 8/00* (2006.01)
- *A61F 2/36* (2006.01)

(52) U.S. Cl.
CPC ........... *A61F 2002/30013* (2013.01); *A61F 2002/30332* (2013.01); *A61F 2002/3694* (2013.01); *A61F 2002/7887* (2013.01); *F04C 2270/0421* (2013.01)

(58) Field of Classification Search
CPC ... A61F 2002/30321; A61F 2002/3694; A61C 2008/0046
See application file for complete search history.

(56) References Cited

U.S. PATENT DOCUMENTS

| | | |
|---|---|---|
| 5,906,644 A | 5/1999 | Powell |
| 2002/0038148 A1 | 3/2002 | Fernandez et al. |
| 2003/0109878 A1 | 6/2003 | Grundei |
| 2005/0214714 A1 | 9/2005 | Wohrle |
| 2007/0060891 A1 | 3/2007 | Skiera et al. |
| 2008/0200995 A1* | 8/2008 | Sidebotham .......... A61F 2/2814 623/28 |
| 2009/0187256 A1 | 7/2009 | Rauguth et al. |
| 2010/0222893 A1 | 9/2010 | Dorr et al. |
| 2011/0257758 A1 | 10/2011 | Smith et al. |

OTHER PUBLICATIONS

Titanium Alloys in Medical Applications, pp. 1-3, retrieved on Dec. 2, 2013 from URL: http://www.azom.com/article.aspx?ArticleID=1794, The Titanium Information Group, UK.

* cited by examiner

PERCUTANEOUS OSSEOINTEGRATED PROSTHETIC IMPLANT SYSTEM

CROSS-REFERENCE TO RELATED APPLICATIONS

This application claims priority to U.S. Provisional Patent Application No. 61/493,914, filed Jun. 6, 2011, U.S. Provisional Patent Application No. 61/594,815, filed Feb. 3, 2012, and U.S. Provisional Patent Application No. 61/622,783, filed Apr. 11, 2012, each of which is hereby incorporated by reference herein in its entirety.

STATEMENT OF GOVERNMENT SUPPORT

This invention was made with United States government support under Grant PR054520 awarded by the Department of Defense, Grant R01HD061014 awarded by the National Institutes of Health, Grant 1RC1 AR058356 awarded by the National Institutes of Health, Grant #RX000262-01 awarded by the Department of Veterans Affairs, Grant #A5-4159RA awarded by the Department of Veterans Affairs, Grant #10091004 awarded by the U.S. Army Medical Research Materiel Command, and Grant #W81XWH-05-1-0628 awarded by the Telemedicine and Advanced Technology Research Center of the U.S. Army's Military Amputee Research Program. The government has certain rights in this invention.

FIELD

This invention generally relates to implant systems for securing a prosthesis to a selected bone of a subject, and, more particularly, to implant systems for modular, osseointegrative securement of a prosthesis to a selected bone of a subject.

BACKGROUND

Amputation of limbs can occur as a result of trauma or surgical intervention. Currently, despite its limitations, socket technology remains the standard of care for attachment and/or docking of exo-prosthetic devices to a residual amputated limb of a patient.

Recent clinical reviews of amputees with socket prosthetics have suggested that between 8 and 50% of amputees with socket prosthetics suffer from one or more dermatological pathologies that require temporary suspension of use of a prosthetic. The inability of these amputees to consistently use their prosthetics represents a significant decrease in their quality of life. In lower limb amputees, the limitations on usage of a prosthetic increase the susceptibility of the amputees to additional co-morbidities. Many pathologies related to current socket prosthetic designs possess interconnected biochemical and biomechanical cues.

High infection rates remain a major limitation of current prosthetic systems. A high infection rate is often associated with the lack of a skin seal at the skin-implant interface that provides an ideal direct path for opportunistic bacterial invasion to the stomal tissue and often results in sinus tract formation. This may subsequently result in deep infection, bone loss and implant removal. Because of the rapid evolution of antibiotic-resistant pathogens as well as the high incidence of methicillin-resistant *Staphylococcus aureus* (MRSA) cases, these infections may not be treatable with conventional antibiotic therapy. Commonly, the outcome is device removal and further loss of limb tissue.

Therefore, what is needed in the art is an inherently adaptable, modular percutaneous osseointegrated prosthetic implant system that permits formation of a seal at the implant-skin interface, reduces dermatological complications associated with socket prosthetics, improves proprioception, extends the periods during which an exo-prosthesis can be worn, and reduces energy expenditure of the amputee wearing the prosthetic, thereby improving the overall quality of life for the amputee.

SUMMARY

The present invention relates to an implant system for securing a prosthesis to a prepared site within a selected bone of a tissue region of a subject. The implant system can include a stem and an abutment. The stem can include an elongate shaft portion and a collar portion. The elongate shaft portion of the stem defines an insertional end of the stem that is received within the prepared site of the selected bone. The elongate shaft portion can have a porous region having a selected length along the longitudinal axis of the stem that promotes bone ingrowth and interdigitation with the host bone tissue, known as osseointegration. The collar portion of the stem defines a second end of the stem and a shoulder surface extending radially outwardly from the outer surface of the elongate shaft portion. The shoulder surface optionally can have a porous region that promotes osseointegration. The collar portion and the elongate shaft portion cooperate to define a central bore of the stem. The ratio between the longitudinal length of the stem and the selected length of the porous region of the elongate shaft portion can range from about 3:1 to about 10:1. At least a portion of the outer surface of the collar portion can be configured to inhibit bio-adhesion.

The abutment includes an attachment element, a post, and a fixation element. The attachment element can be securely attached to the stem such that the abutment is operatively coupled to the stem. The post can have an insertional first end portion, an opposed second end portion, and a central portion between the first and second end portions. Upon attachment of the attachment element to the stem, the insertional first end portion can be operatively positioned relative to the stem, and the opposed second end can be configured for selective secure attachment to the prosthesis. At least a portion of the outer surface of the post can be configured to inhibit bio-adhesion. The fixation element can be secured to the outer surface of the post at a selected position along the longitudinal axis of the abutment. The fixation element can extend radially outwardly relative to the outer surface of adjoining portions of the post, thereby defining a fixation surface configured to abut tissue of the subject proximate the prepared site within the selected bone. The fixation element optionally can be formed of a porous material.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

FIG. 4 depicts an exemplary configuration of the tapered surfaces relative to a fixation element as described herein. FIG. 5 depicts the respective orientation angles of exemplary first and second tapered surfaces as described herein.

FIGS. 6A and 6B depict exemplary collar portions having tapered elongate portions, while FIG. 6C depicts an exemplary collar portion having an elongate portion with a substantially consistent diameter.

FIGS. 7A-7B depict exemplary stems having selectively attachable collar portions and elongate shaft portions, while FIG. 7C depicts an exemplary stem having only a collar portion.

DETAILED DESCRIPTION

Figure 1:
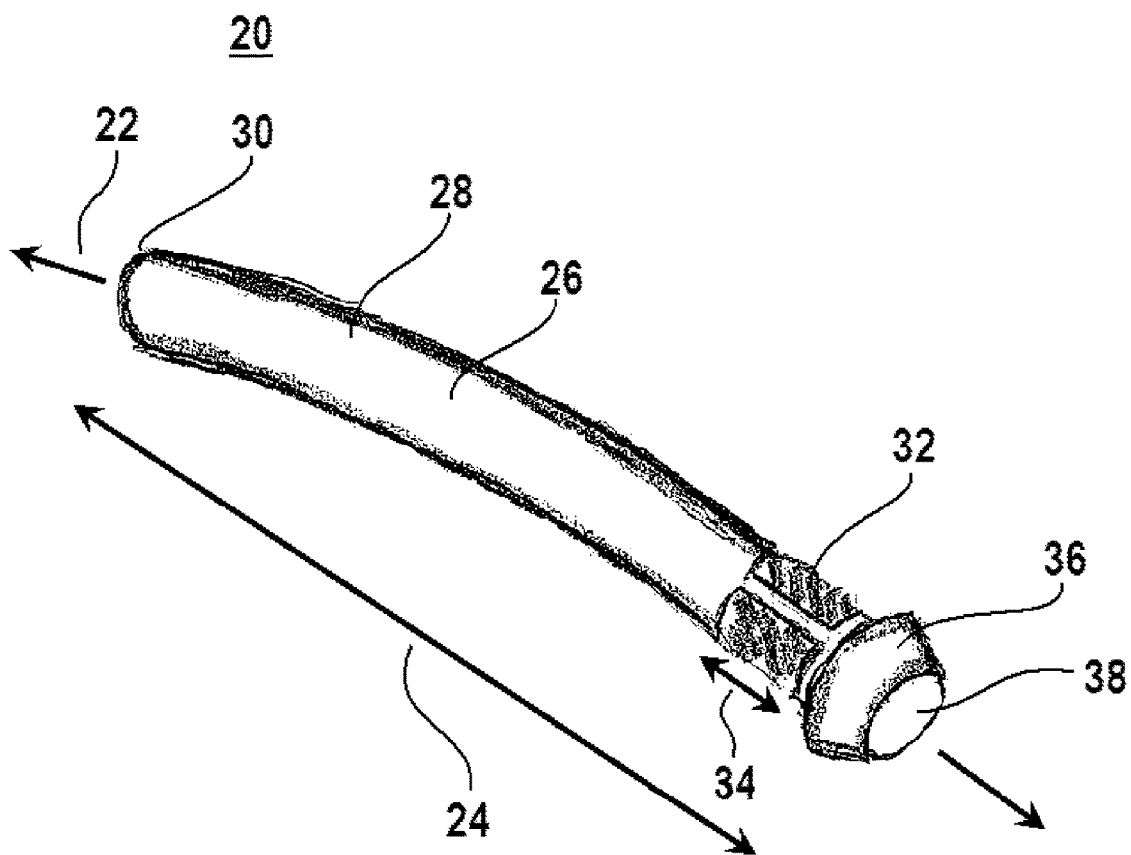
FIG. 1 depicts an exemplary stem for use in an implant system as described herein.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a porous region" can include two or more such prostheses unless the context indicates otherwise.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

By a "subject" is meant an individual. The term subject can include humans and can also include small or laboratory animals as well as primates. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included.

As used herein, the term "insertional" refers to the end of a first element that is configured for insertion into a second element. For example, as used herein, an "insertional" end of an element can be configured for insertion into a prepared site within a bone or for insertion into an implant stem.

As used herein, the term "ultra-low friction surface" refers to a surface comprising or coated with one or more materials that are configured to inhibit adhesion and/or adsorption between the surface and other materials. For example, "ultra-low friction surfaces" as described herein permit little if any in-growth, integration, and/or adhesion between the surface and biological tissues, biological fluids, and bacteria. It is contemplated that the reduced bio-adhesion permitted by the "ultra-low friction surfaces" as described herein can permit thorough post-operative drainage for improved wound healing, ease "at-home" cleaning, and reduce the incidence of infection. Exemplary ultra-low friction surfaces include surfaces that comprise or are coated with ultra-hydrophobic materials. Additional exemplary ultra-low friction surfaces include, for example and without limitation, gold, ceramics, polymers (e.g., ultra high molecular weight polyethylene), diamond-like carbon (DLC) coatings, oxidized zirconium, titanium nitride, and the like. It is contemplated that exemplary "ultra-low friction surfaces" as described herein can have coefficients of friction that are less than or equal to about 0.6 and, more preferably, less than or equal to about 0.01 (approaching superlubricity).

Disclosed herein are implants, implant systems, and methods for securing a prosthesis to a limb of a subject. It is contemplated that the disclosed implants, implant systems, and methods can be used to permit integration of bone and skin of the subject into an implant to which a prosthesis is operably attached. It is further contemplated that the disclosed implants, implant systems, and methods can permit formation of a seal between the skin of the subject and the implant, thereby minimizing the possibility of infection at the interface between the implant and the skin of the subject. It is still further contemplated that the disclosed implants, implant systems, and methods can minimize post-implantation migration of the skin of the subject, thereby reducing the likelihood of formation of a pocket between the skin of the subject and the implant. In particular applications, it is contemplated that the disclosed implants, implant systems, and methods can be used to bring military, veterans and civilian lower extremity amputees back to pre-amputation/ improved activity levels. Generally, it is contemplated that the above-mentioned objectives can be achieved through optimized selection of various characteristics of the implant, such as, for example, characteristics of a stem and/or abutment as described herein, to achieve a desired arrangement and/or orientation of the implant relative to the bone and surrounding tissue of the subject, as well as a desired attachment between the implant and a prosthesis.

Referring to FIGS. 1-5, an implant system 10 is provided for securing a prosthesis to a selected bone of a tissue region of a subject, such as, for example, a selected bone within an upper or lower extremity of a subject. As used herein, the term "prepared site" refers to any location within a selected bone of a subject that is prepared to receive an implant, such as, for example, the stem implants described herein, using conventional surgical methods. In exemplary aspects, the prepared site can be an intramedullary cavity of a selected bone. In additional exemplary aspects, the selected bone can be a femur of the subject. However, it is contemplated that the disclosed methods, systems, and steps and components thereof can be used with any bone within a tissue region of a subject, including, for example, any bone within an upper or lower extremity of a subject. It is contemplated that the implant system 10 can be used to secure a prosthesis to a prepared site within the selected bone. In exemplary aspects, the implant system 10 can comprise a stem 20 and an abutment 50. In these aspects, the stem 20 can be configured for secure attachment to the selected bone, and the abutment 50 can be configured for secure attachment to the stem. Following attachment of the abutment 50 to the stem 20, the abutment can be configured for secure attachment to the prosthesis.

Figure 3:
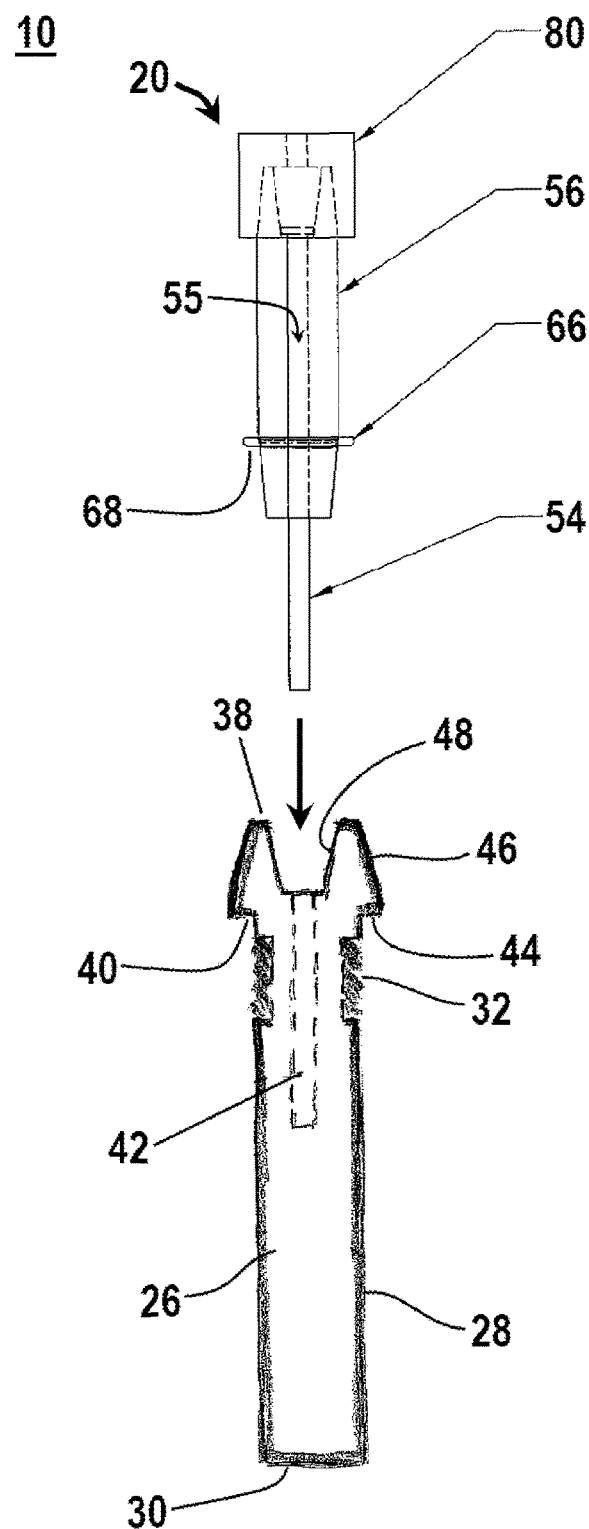
FIG. 3 depicts an exemplary implant system having a stem and an abutment as described herein.

In one aspect, as shown in FIGS. 1 and 3, the stem 20 can have a longitudinal axis 22 and a longitudinal length 24. In this aspect, it is contemplated that the longitudinal length 24 of the stem 20 can range from about 1 inch to about 10 inches. In femoral prosthesis applications, it is contemplated that the longitudinal length 24 of the stem 20 can range from about 2 inches to about 10 inches. In exemplary femoral prosthesis applications, it is contemplated that the longitudinal length 24 of the stem can range from about 6 inches to about 10 inches. In another aspect, the stem 20 can optionally comprise an elongate shaft portion 26 defining an insertional end 30 of the stem and having an outer surface 28 that defines an outer diameter of the stem. In this aspect, the insertional end 30 of the stem 20 can be configured for receipt within the prepared site within the selected bone. It is contemplated that the stem 20 can be securely received within the prepared site such that the longitudinal axis 22 of the stem is substantially axially aligned with the longitudinal axis of the selected bone. In one aspect, the stem 20 can comprise one or more metallic materials, including, for example and without limitation, medical grade titanium, cobalt chrome, and the like. In exemplary aspects, at least a portion of the outer surface 28 of the elongate shaft portion 26 of the stem 20 can be grit-blasted using conventional methods to impart desired surface roughness to the elongate shaft portion, thereby improving bone attachment. Optionally, the outer surface 28 of the elongate shaft portion 26 of the stem 20 can comprise at least one flute, at least one rib, and/or at least one slot configured to promote fixation with the selected bone. In exemplary aspects, it is contemplated that the outer surface 28 of the elongate shaft portion 26 can comprise a plurality of spaced ribs oriented substantially perpendicularly to the longitudinal axis 22 of the stem 20. It is contemplated that the outer diameter of the stem 20 can range from about 0.25 inches to about 1.00 inch and, more preferably, from about 0.5 inches to about 0.75 inches.

Optionally, in exemplary aspects, the elongate shaft portion 26 of the stem 20 can be configured to mimic physiological properties of the anatomical bow within a native bone, thereby reducing and/or limiting torsional displacement of the stem following implantation, and improving both short-term and long-term performance of the stem. It is further contemplated that the elongate shaft portion 26 of the stem 20 can be configured to prevent proximal implant binding and to limit subsequent distal bone atrophy due to stress shielding. In exemplary aspects, when the selected bone is a femur, it is contemplated that the selected bone can be configured for medullary bowing along a radius of curvature ranging from about 100 mm to about 1,400 mm and for cortical bowing ranging from about 100 mm to about 1,700 mm. In these aspects, it is contemplated that the elongate shaft portion 26 of the stem 20 can be configured for bowing along a radius of curvature ranging from about 600 mm to about 900 mm, and more preferably, from about 700 mm to about 800 mm. It is further contemplated that the amount of engaged/implanted device curvature can be reliant on the total length of the stem and the optimal seating location of the stem following transection. In exemplary femoral applications, it is contemplated that the optimal seating location of the stem following transection can be within a distance of about 16 mm between a distal end of the transected femur and a knee joint articulation space. In these applications, it is contemplated that the radius of curvature of the stem can be determined and/or calculated by assuming that the length of the stem at least substantially corresponds initially to the length of the intact/whole femur. In exemplary aspects, it is contemplated that the amount of curvature for the engaged/implanted stem can be substantially equal to the amount of curvature (i.e. curved arc length) present in the length of the remainder of the shaft that is positioned below/inferior the greater trochanter and above/superior the distal end of the transection/bone resection cut. For non-femoral applications (when the selected bone is not a femur), it is contemplated that similar processes can be followed to determine desired medullary bowing characteristics for the stem.

In a further aspect, the elongate shaft portion 26 can comprise a porous region 32 having a selected length 34 along the longitudinal axis 22 of the stem. In an exemplary aspect, the ratio between the longitudinal length 24 of the stem 20 and the selected length 34 of the porous region 32 can range from about 1.5:1 to about 20:1 and, more preferably, range from about 4:1 to about 8:1. Thus, it is contemplated that, in exemplary aspects, the selected length 34 of the porous region 32 can range from about 0.1 inches to about 4 inches and, more preferably, from about 0.5 inches to about 3 inches.

In additional aspects, it is contemplated that the modular characteristics of the stem 20 can provide a platform for further optimization of the design of the stem without the need for significant surgical intervention. For example, it is contemplated that the limited dimensions of the porous region can be configured to permit removal and/or revision of the stem with minimal loss or destruction of residual bone. It is further contemplated that, in the event of a bone infection following implantation of the stem, the stem can be removed, the surgically revised site can be allowed to drain, and a therapeutic treatment regimen can be executed without significant tissue loss or harm to the subject.

In another exemplary aspect, the porous region 32 of the elongate shaft portion 26 can be recessed relative to the outer surface 28 of adjoining portions of the elongate shaft portion. Optionally, in this aspect, the porous region 32 can comprise a recessed portion of the outer surface 28 of the elongate shaft portion 26 that is coated with a porous material using known methods for coating a substrate. It is contemplated that the porous region 32 can optionally comprise a continuous circumferential layer of porous material. Alternatively, it is contemplated that the porous region 32 can optionally comprise a plurality of porous sections that are spaced about an operative circumference of the porous region. Optionally, the outer surface 28 of the elongate shaft portion 26 can define the outer boundaries of the respective spaced porous sections of the porous region 32. For example, it is contemplated that the outer surface 28 of the elongate shaft portion 26 can comprise one or more narrow regions that extend contiguously through the porous region 32 along the longitudinal axis 22 of the stem 20, with each narrow region of the one or more narrow regions forming a boundary between adjacent porous sections. Optionally, in another aspect, the portion of the elongate shaft portion 26 corresponding to the porous region 32 can comprise a separate structure having at least an outer surface of porous material such that the outer surface 28 of the elongate shaft portion is discontinuous at the position of the porous region, with the elongate shaft portion being divided into distinct sections on opposite sides of the porous region and the porous region 32 connecting the sections of the elongate shaft portion. It is contemplated that the porous region 32 of the elongate shaft portion 26 can be formed using known milling techniques.

In one aspect, the porous region 32 can comprise porous titanium. In this aspect, it is contemplated that the porous region 32 can comprise substantially pure porous titanium to thereby improve osseointegration by bone in-growth and interdigitations along the length of the porous region. However, it is contemplated that other medical grade porous metals, as well as porous polymers and ceramics, can be used as described herein. In exemplary aspects, the porous region 32 of the elongate shaft portion 26 can have a thickness ranging from about 0.5 mm to about 2.0 mm. In additional exemplary aspects, the porosity of the porous region 32 of the elongate shaft portion 26 can range from about 40% to about 80% and, more preferably, from about 50% to about 70%. In these aspects, it is contemplated that the size of each pore of the porous region 32 can range from about 25 μm to about 1,000 μm and, more preferably, from about 20 μm to about 400 μm. However, as one will appreciate, it is contemplated that the desired porosity and pore size for the porous region 32 can be selectively varied depending upon, for example and without limitation, the host bone stock/condition, amputation causality, the age of the patient, the residual limb length, the time since initial injury, the time since amputation, the vascular health of the patient, and other factors.

It is contemplated that, upon secure receipt of the stem 20 within the prepared site, the porous region 32 of the stem can be configured to promote integration and ingrowth of the selected bone of the subject into the stem. It is further contemplated that such osseointegration (between the selected bone and the porous region 32 of the stem 20) can lead to improvement in the post-surgery quality of life of the subject through improved proprioception (i.e., dynamic exoprosthesis load sensation) and gait efficiency (i.e., improved physiologic energy expenditure).

In an additional aspect, the stem 20 can comprise a collar portion 36 that has an outer surface 46 and defines a second end 38 of the stem. In this aspect, the second end 38 of the stem 20 is spaced from the insertional end 30 of the stem along the longitudinal axis 22 of the stem. In one aspect, at least a portion of the collar portion 36 can have an outer diameter that is greater than the outer diameter of the elongate shaft portion 26. In this aspect, it is contemplated that the collar portion 36 can define a shoulder surface 40 extending radially outwardly from the outer surface 28 of the elongate shaft portion 26. It is contemplated that the shoulder surface 40 can be configured to form a flush interface and/or seal with the selected bone. It is further contemplated that the flush interface and/or seal formed between the shoulder surface 40 and the selected bone can permit transfer of ground reaction forces substantially directly to the skeletal system of the subject, thereby preventing bone atrophy. In exemplary aspects, the shoulder surface 40 can be substantially flat and extend substantially perpendicularly relative to the longitudinal axis 22 of the stem 20. However, it is contemplated that the shoulder surface 40 can be a chamfered surface or have another surface shape, provided the shoulder surface permits formation of a flush interface with the selected bone. It is further contemplated that the shoulder surface can be shaped to substantially conform to the shape of adjacent tissues within the subject. In exemplary aspects, the shoulder surface 40 can have a substantially circular cross-sectional profile about the longitudinal axis 22 of the stem 20. However, it is also contemplated that the an elliptical or other cross-sectional profile that permits formation of a flush interface with the selected bone and provides desired support to the selected bone. Optionally, at least a portion of the outer surface 46 of the collar portion 36 can comprise a porous material as described herein.

Optionally, the outer surface 46 of the collar portion 36 can be outwardly tapered, sloped, and/or curved moving along the longitudinal axis 22 of the stem 20 from the second end 38 of the stem to the shoulder surface 40. In this aspect, it is contemplated that the taper, slope, and or curvature of the outer surface 46 of the collar portion 36 can be configured to substantially conform to the shape of adjacent tissue structures within the subject.

In exemplary aspects, the shoulder surface 40 can comprise at least one porous region 44. In these aspects, the at least one porous region 44 of the shoulder surface 20 can comprise a medical grade porous metal, polymer, ceramic, and the like. In one aspect, the at least one porous region 44 of the shoulder surface can 40 comprise, for example and without limitation, porous titanium. It is contemplated that the at least one porous region 44 of the shoulder surface 40 can be in the form of a porous coating applied to the shoulder surface using known coating methods. Alternatively, it is contemplated that the at least one porous region 44 of the shoulder surface 40 can be formed using known milling techniques. In exemplary aspects, the at least one porous region 44 of the shoulder surface 40 can have a thickness ranging from about 0.5 mm to about 2.0 mm. In additional exemplary aspects, the porosity of the at least one porous region 44 of the shoulder surface 40 can range from about 40% to about 70% and, more preferably, from about 50% to about 80%. In these aspects, it is contemplated that the size of each pore of the at least one porous region 44 of the shoulder surface 40 can range from about 25 μm to about 1,000 μm and, more preferably, from about 30 μm to about 400 μm. It is contemplated that the at least one porous region 44 of the shoulder surface 30 of the collar portion 36 can be configured to facilitate—and increase—bone integration, thereby ensuring contiguous load transmission between the implant system 10 and the distal end of the bone. It is further contemplated that appropriately scaled load transmission at this interface can prevent bone resorption due to stress shielding at the distal bone end of the transected bone and can promote bone hypertrophy more proximally.

Optionally, in various aspects, the porous region 32 of the elongate shaft portion 26 of the stem 20 can be spaced along the longitudinal axis 22 of the stem from the shoulder surface 40 of the collar portion 36. In these aspects, it is contemplated that the space between the porous region 32 of the elongate shaft portion 26 of the stem 20 and the shoulder surface 40 can define a resection cutting plane at the most distal portion of the residual limb. It is further contemplated that, should resection be required, the introduction of a cut at the extreme distal end of the bone can help avoid the loss of additional residual limb length. It is still further contemplated that, once the circumferential cut is made and tension is applied to the second end 38 of the stem 20, the engagement at the bone-recessed porous region interaction plane can be substantially weakened such that the stem 20 can break loose from the bone. It is still further contemplated that cleavage along the bone-porous region interface can allow the stem to come out "smoothly" without the destruction of remaining cortical bone.

In a further aspect, at least a portion of the outer surface 46 of the collar portion 36 can be configured to inhibit bioadhesion. In this aspect, the portion of the outer surface 46 of the collar portion 36 that is configured to inhibit bioadhesion can comprise an ultra-low friction surface as defined above. It is contemplated that the portion of the outer surface 46 of the collar portion 36 comprising an ultra-low friction surface can include the second end 38 of the stem 20.

In another aspect, the portion of the outer surface 46 of the collar portion 36 that is configured to inhibit bioadhesion can comprise a highly polished surface, which possesses a low coefficient of friction. In this aspect, it is contemplated that the portion of the outer surface 46 of the collar portion 36 comprising the highly polished surface can include the second end 38 of the stem 20.

In exemplary aspects, it is contemplated that the highly polished surfaces described herein can have $R_t$, or maximal peak to valley (P-V), values from profilometry and/or white light interferometry analysis that are less than about 20 µm, are, more preferably, less than about 5 µm, and are, most preferably, less than about 3 µm. In further exemplary aspects, the highly polished surfaces described herein can have $R_t$, or maximal peak to valley (P-V), values from profilometry and/or white light interferometry analysis that are less than about 2 µm. It is further contemplated that these values can be pre-determined, or designed for, by an appropriate combination of milling bit and/or surface coating. Suitable profilometry analyses can be conducted by sweeping and/or sliding a probe having a specific geometry over the surface to determine the relative roughness of the surface material. White light interferometry, an optical technique, can be employed to use light refraction and optics (and/or physics) to determine the relative roughness of a given surface material. It is contemplated that both profilometry and interferometry, as well as other known comparable techniques, can be used in conjunction with one another to characterize the surfaces of the various elements of the disclosed implant system. Optionally, in exemplary aspects, it is contemplated that the ultra-low friction surfaces described herein can also have $R_t$, or maximal peak to valley (P-V), values from profilometry and/or white light interferometry analysis that are less than about 20 µm, are, more preferably, less than about 5 µm, and are, most preferably, less than about 3 µm. In further exemplary aspects, the ultra-low friction surfaces described herein can have $R_t$, or maximal peak to valley (P-V), values from profilometry and/or white light interferometry analysis that are less than about 2 µM.

In another aspect, the collar portion 36 and the elongate shaft portion 26 can cooperate to define a central bore 42 extending along at least a portion of the longitudinal length 24 of the stem 20. In this aspect, it is contemplated that the collar portion 36 can define an inner surface 48 extending from the second end 38 of the stem 20 along at least a portion of the longitudinal length 24 of the stem. As shown in FIG. 3, it is further contemplated that the inner surface 48 can substantially terminate into the central bore 42. In exemplary aspects, the inner surface 48 of the collar portion 36 can be inwardly tapered along the longitudinal axis 22 of the stem 20 from the second end 38 of the stem toward the insertional end 30 of the stem. In these aspects, the inner surface 48 of the collar portion 36 can comprise a conventional Morse taper. It is contemplated that the inner surface 48 of the collar portion 36 can be tapered inwardly relative to the longitudinal axis 22 of the stem 20 at an angle ranging from about 3 degrees to about 7 degrees and, more preferably, from about 4 degrees to about 6 degrees. In exemplary aspects, the angle of the taper of the inner surface 48 of the collar portion 36 can substantially correspond to the angle of the taper of the corresponding portion of the abutment 50 as described herein. It is contemplated that the inner surface 48 of the collar portion 36 can be configured to serve as a "female" taper that receives a portion of the abutment 50 as further described herein. In an exemplary aspect, the central bore of the stem can be a threaded bore. However, it is contemplated that the bore can have any shape and/or geometrical configuration that permits secure attachment to an abutment as described herein.

Figure 2:
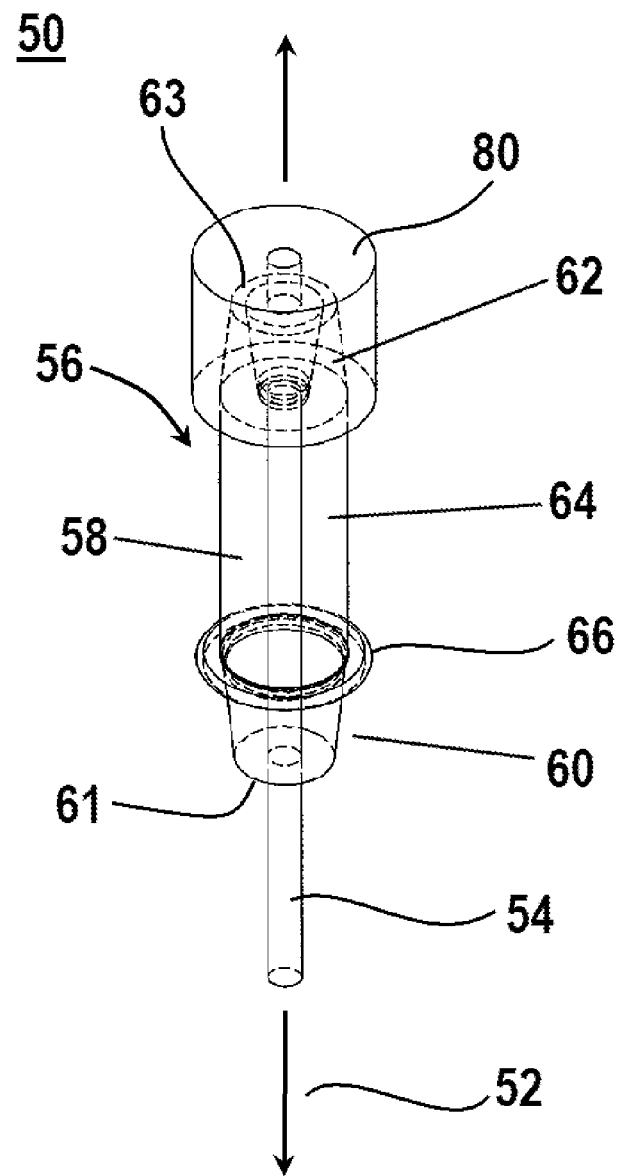
FIG. 2 depicts an exemplary abutment for use in an implant system as described herein.

In exemplary aspects, as shown in FIGS. 2-3, the abutment 50 can comprise a longitudinal axis 52, an attachment element 54, a post 56, and a fixation element 66. In these aspects, the attachment element 54 can be configured for secure attachment to the stem 20. In one aspect, the attachment element 54 can comprise a threaded bolt configured for receipt within the central bore 42 of the stem 20. However, it is contemplated that the attachment element 54 can have any shape and/or geometrical configuration that permits secure, complementary receipt of the attachment element within the central bore 42 of the stem 20. In an exemplary aspect, the abutment 50 can define a central bore 55 extending along the entire longitudinal length of the abutment. In this aspect, it is contemplated that the attachment element 54 can be positioned within the central bore 55 of the abutment 50 such that, upon secure attachment between the stem 20 and the abutment 50, the attachment element is securely positioned within the central bore of the stem and the central bore of the abutment, thereby providing stability to the abutment. It is contemplated that the attachment element 54 can be securely positioned within the central bore 42 of the stem 20 such that the longitudinal axis 52 of the abutment 50 is substantially aligned with the longitudinal axis 22 of the stem.

In a further aspect, the post 56 of the abutment 50 can have an outer surface 58, an insertional first end portion 60, an opposed second end portion 62, and a central portion 64 positioned between the first end portion and the second end portion. In this aspect, it is contemplated that the insertional first end portion 60 can comprise an insertional first end 61, and the second end portion 62 can comprise an opposed second end 63 spaced along the longitudinal axis 52 of the abutment 50 from the insertional first end. It is further contemplated that the post 56 can be generally cylindrical. In another aspect, the post 56 can be operatively coupled to the attachment element 54 such that, upon secure attachment of the attachment element to the stem 20, the insertional first end portion 60 of the abutment 50 is configured for operative positioning relative to the stem 20, and the opposed second end portion 62 of the abutment is configured for selective secure attachment to the prosthesis.

In another aspect, the outer surface 58 of the post 56 of the abutment 50 can comprise one or more tapered surface portions. In this aspect, it is contemplated that the one or more tapered surface portions can substantially consistent tapers. Alternatively, it is further contemplated that the one or more tapered surface portions can have different tapers, such as, for example and without limitation, increasing, decreasing, or variable tapers. Optionally, the one or more tapered surface portions can be spaced apart along the longitudinal axis 52 of the abutment 50. In exemplary aspects, the insertional end portion 60 of the abutment 50 can comprise a first tapered surface 70 that is inwardly tapered along the longitudinal axis 52 of the abutment 50 moving away from the central portion 64 of the post 56 and toward the insertional end 61 of the post. In these aspects, it is contemplated that the first tapered surface 70 of the insertional end portion 60 of the abutment 50 can be a "male" taper that is configured for complementary receipt within the inner surface 48 of the collar portion 36 of the stem 20. It is further contemplated that the first tapered surface 70 can be oriented relative to the longitudinal axis 52 of the abutment 50 at an angle 71 ranging from about 0.25 degrees to about 3 degrees and, more preferably from about 1 degree to about 3 degrees.

Figure 4:
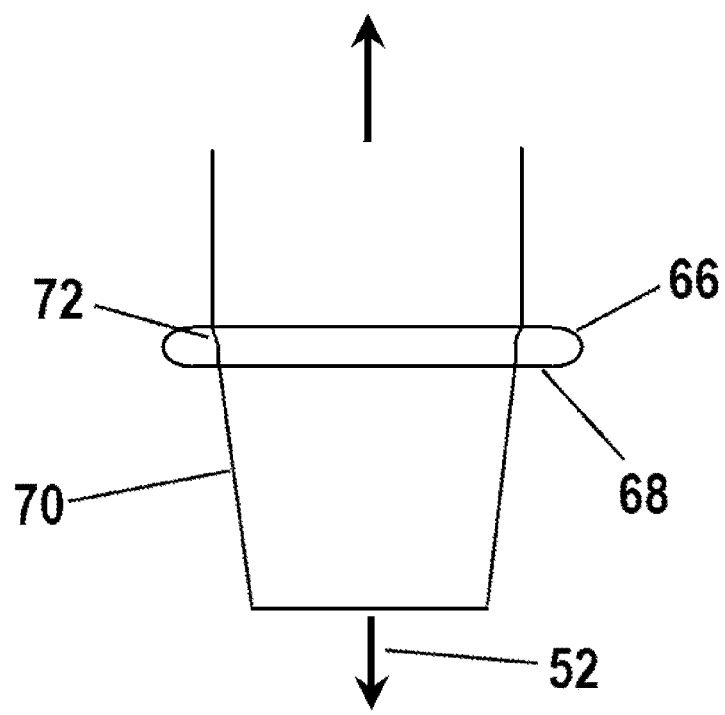
FIGS. 4-5 are close-up views of exemplary tapered surfaces of a post of an abutment as described herein.
Figure 5:
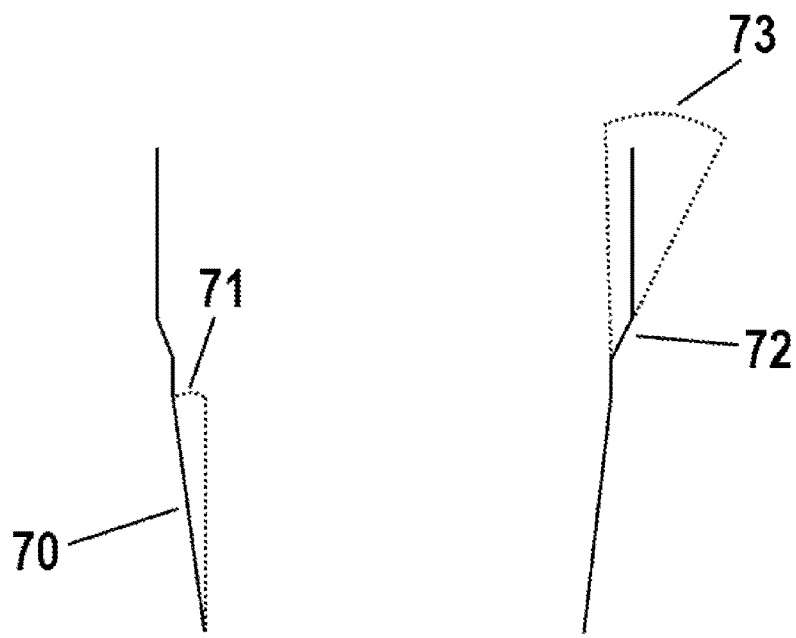

In a further aspect, as shown in FIGS. 4-5, the outer surface 58 of the post 56 can define a second tapered surface 72 positioned proximate the interface between the insertional end portion 60 of the post and the central portion 64 of the post. In exemplary aspects, the second tapered surface 72 can be inwardly tapered along the longitudinal axis 52 of the abutment 50 from the central portion 64 of the post 56 toward the insertional end 61 of the post. In these aspects, the second tapered surface 72 can be oriented relative to the longitudinal axis 52 of the abutment at an angle 73 ranging from about 1.5 degrees to about 5 degrees. Thus, as demonstrated in FIG. 5, it is contemplated that the second tapered surface 72 can have an orientation angle 73 relative to the longitudinal axis of the abutment that is about 1 degree to about 1.5 degrees greater than an orientation angle 71 of the first tapered surface 70 relative to the longitudinal axis 52 of the abutment 50. In another exemplary aspect, the second tapered surface 72 can be configured to engage the fixation surface of a fixation element as described herein (see FIG. 4). Optionally, the first and second tapered surfaces 70, 72 can be spaced apart along the longitudinal axis 52 of the abutment 50 (see FIG. 4). Alternatively, the first and second tapered surfaces 70, 72 can be substantially contiguous along the longitudinal axis 52 of the abutment 50.

In exemplary aspects, at least a portion of the outer surface 58 of the post 56 can be configured to inhibit bio-adhesion. In one aspect, the portion of the outer surface 58 of the post 56 that is configured to inhibit bio-adhesion can be an ultra-low friction surface as defined above. In this aspect, it is contemplated that the central portion 64 of the post 56 can be an ultra-low friction surface. In configurations of the post 56 where the second tapered surface 72 is spaced apart from the first tapered surface 70, it is also contemplated that the portion of the outer surface of the post positioned between the first and second tapered surfaces can be an ultra-low friction surface.

In another aspect, the portion of the outer surface 58 of the post 56 that is configured to inhibit bio-adhesion can be a highly polished surface. In this aspect, it is contemplated that the central portion 64 of the post 56 can be a highly polished surface. In configurations of the post 56 where the second tapered surface 72 is spaced apart from the first tapered surface 70, it is also contemplated that the portion of the outer surface 58 of the post positioned between the first and second tapered surfaces can be a highly polished surface.

In an additional aspect, the abutment 50 can comprise a fixation element 66 secured to the outer surface 58 of the post 56 at a selected position along the longitudinal axis 52 of the abutment 50. In this aspect, it is contemplated that the fixation element 66 can extend radially outwardly relative to the outer surface 58 of adjoining portions of the post 56. It is further contemplated that the portion of the fixation element 66 that extends radially outwardly relative to the outer surface 58 of the post can define a fixation surface 68. In exemplary aspects, the fixation surface 68 can be substantially flat and extend substantially perpendicularly relative to the longitudinal axis 52 of the abutment 50. However, it is contemplated that the fixation surface 68 can be a chamfered surface, a curved surface, or can have another surface shape, provided the fixation surface 68 is configured to form an interface with at least a portion of the soft tissue of the subject proximate the prepared site within the selected bone. It is still further contemplated that the fixation surface 68 defined by the fixation element 66 can be configured to abut soft tissue of the subject proximate the prepared site within the selected bone. It is still further contemplated that the fixation element 66 can be configured to promote fixation and inhibit rotation/destabilization of soft tissue proximate the prepared site such that inflammation is reduced and healing is expedited. In exemplary aspects, the fixation element surface 66 can be welded to the outer surface 58 of the post 56 at the selected position. In these aspects, it is contemplated that the fixation element 66 can be cold-welded to the outer surface 58 of the post 56 using known techniques. It is further contemplated that the selected position of the fixation element 66 can be varied depending on the particular positioning and configuration of the stem 20 and prosthesis to which the abutment 50 is attached.

It is contemplated that the attachment element 54 and the post 56 can comprise conventional surgical-quality metallic materials, including, for example and without limitation, titanium, cobalt chrome, and the like. It is contemplated that the fixation element 66 can comprise any metal, polymer, or ceramic material having a desired porosity. In exemplary aspects, the desired porosity of the fixation element 66 can range from about 40% to about 70%. In these aspects, it is contemplated that the size of each pore of the fixation element 66 can range from about 25 µm to about 1,000 µm and, more preferably, from about 30 µm to about 400 µm.

In another aspect, it is contemplated that the fixation element 66 can comprise a porous material, such as, for example, a porous metal material, that is different from the metallic material from which the post 56 is formed. For example, it is contemplated that the fixation element 66 can comprise porous titanium, while the post 56 can comprise cobalt chrome. It is contemplated that the use of a fixation element 66 and a post 56 comprising two different metal materials, such as, for example, cobalt-chrome and titanium, can produce an advantageous electro-static surface interaction that will improve design element cohesion. It is further contemplated that the porosity of the fixation element 66 can improve soft-tissue outcomes by reducing relative motion between the implant system 10 and the surrounding soft tissue to decrease the inflammatory response of the subject and to reduce or prevent infection through the promotion of soft-tissue capture, which helps maintain a biological barrier to the external environment.

Optionally, in another aspect, the implant system 10 can further comprise an overload protection mechanism 80. In this aspect, it is contemplated that the overload protection mechanism 80 can comprise any conventional means for isolating an osseointegrated component, such as the stem, from the external environment such that the selected bone of the subject is protected from catastrophic loads experienced by portions of the implant system external to the body of the subject, such as, for example, the prosthesis. As shown in FIGS. 2-3, it is further contemplated that the overload protection mechanism 80 can be operatively coupled to the second end portion 62 of the post 56.

Optionally, it is contemplated that the collar portion 36 can be integrally formed with the elongate shaft portion 26 of the stem 20. Alternatively, in further optional aspects, the collar portion 36 can be configured for selective, detachable engagement with the elongate shaft portion 26 of the stem. For example, in these aspects, it is contemplated that the collar portion 36 can define a cavity configured to receive at least a portion of the elongate shaft portion 26 of the stem 20. It is further contemplated that the elongate shaft portion 26 of the stem 20 can be configured for positioning within the cavity of the collar portion 36 in a jam fit, press fit, or other frictional fit.

In exemplary aspects, as shown in FIGS. 6A-7C, when the collar portion 36 is not integrally formed with the elongate shaft portion 26 of the stem 20, the collar portion 36 can have a longitudinal axis 37 and can comprise an elongate portion 39 extending from the shoulder surface 40 of the collar portion 36 along the longitudinal axis of the collar portion in an insertional direction (away from the second end 38 of the stem 20). In these aspects, it is contemplated that the elongate portion 39 of the collar portion 36 can define at least a portion of the cavity of the collar portion that is configured to receive the elongate shaft portion 26 of the stem 20. Optionally, in these aspects, it is further contemplated that at least a portion of the elongate portion 39 of the collar portion 36 can comprise a porous material as described herein. In some exemplary optional aspects, it is contemplated that the elongate shaft portion 26 of the stem 20 can be non-porous while the elongate portion 39 of the collar portion 36 can comprise a porous region, with the porous region of the elongate portion of the collar portion being positioned relative to the shoulder surface 40 in substantially the same manner as porous region 32 of the elongate shaft portion (as described above). Optionally, in other aspects, the elongate shaft portion 26 of the stem 20 and the elongate portion 39 of the collar portion 36 can each comprise at least one porous region. In further aspects, it is contemplated that at least a portion of the elongate portion 39 of the collar portion 36 can be grit-blasted to impart desired surface roughness to the stem 20 and thereby increase the strength of the attachment between the stem and the selected bone of the subject. Optionally, it is contemplated that at least a portion of the elongate portion 39 of the collar portion 36 can be fluted, ribbed, and/or slotted to improve fixation between the stem 20 and the selected bone of the subject.

In additional optional aspects, the elongate portion 39 of the collar portion 36 can have a substantially constant diameter and, thus, can be substantially cylindrical. Alternatively, in other optional aspects, the elongate portion 39 of the collar portion 36 can have a variable diameter along the longitudinal axis 37 of the collar portion 36 and, thus, can be tapered. In these aspects, it is contemplated that the elongate portion 39 of the collar portion 36 can be inwardly tapered along the longitudinal axis 37 of the collar portion 36 in an insertional direction (away from the second end 38 of the stem 20). It is further contemplated that the elongate portion 39 of the collar portion 36 can be inwardly tapered at an angle ranging from about 1° to about 30° relative to the longitudinal axis of the collar portion 36. In one aspect, it is contemplated that the taper of the elongate portion 39 of the collar portion 36 can be substantially consistent along the longitudinal axis 37 of the collar portion. However, in other aspects, it is contemplated that the taper of the elongate portion 39 of the collar portion 36 can be compound, such as, for example and without limitation, a taper comprising two or more steps of consistent, increasing, decreasing, or variable taper.

It is contemplated that at least one of (a) the longitudinal length of the elongate shaft portion 26 of the stem 20, (b) the longitudinal length of the elongate portion 39 of the collar portion 36 of the stem, (c) the taper of the elongate portion of the collar portion of the stem, (d) the diameter of the elongate shaft portion of the stem, and (e) the diameter of the elongate portion of the collar portion of the stem can be selectively varied depending upon the characteristics of the selected bone and the prepared site, including, for example and without limitation, the amputation level. It is further contemplated that, the more extensive the level of amputation is, the less the diameter of the elongate shaft portion 26 and the elongate portion 39 of the collar portion 36 will generally be.

Figure 6A:
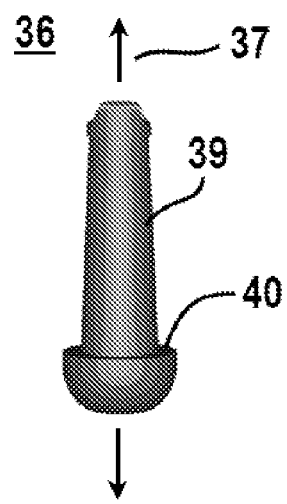
FIGS. 6A-6C depict exemplary collar portions of a stem as described herein.
Figure 6B:
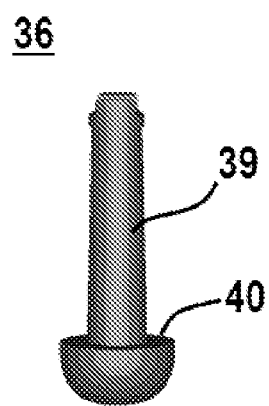
Figure 6C:
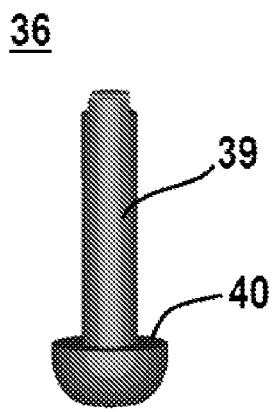

In an exemplary aspect, and with reference to FIG. 6A, when the stem 20 is used for a 35% amputation level, it is contemplated that the diameter of the elongate portion of the collar portion proximate the shoulder surface 40 can be about 18 mm, while the diameter of the elongate portion of the collar portion proximate an opposed, insertional end of the elongate portion can be about 14 mm. In this aspect, it is contemplated that the diameter of the elongate shaft portion of the stem can be about 12 mm. In another exemplary aspect, and with reference to FIG. 6B, when the stem 20 is used for a 50% amputation level, it is contemplated that the diameter of the elongate portion of the collar portion proximate the shoulder surface 40 can be about 14 mm, while the diameter of the elongate portion of the collar portion proximate an opposed, insertional end of the elongate portion can be about 12 mm. In this aspect, it is contemplated that the diameter of the elongate shaft portion of the stem can be about 10 mm. In still another exemplary aspect, and with reference to FIG. 6C, when the stem 20 is used for a 65% amputation level, it is contemplated that the diameter of the elongate portion of the collar portion can be about 12 mm substantially consistently along the longitudinal length of the elongate portion. In this aspect, it is contemplated that the diameter of the elongate shaft portion of the stem can be about 12 mm.

In exemplary aspects, for femoral applications, the longitudinal length of the elongate shaft portion 26 of the stem 20 can range from about 40 mm to about 150 mm, and, more preferably, range from about 75 mm to about 125 mm.

In additional exemplary aspects, it is contemplated that the diameter of the shoulder surface 40 of the collar portion 36 can be about 25 mm and that the longitudinal length of the elongate portion 39 of the collar portion can be about 40 mm.

In various aspects, it is contemplated that the elongate shaft portion 26, when positioned within a cavity of a collar portion 36 as described herein, can be configured to extend through the cavity of the collar portion beyond the second end 38 of the stem 20. In these aspects, it is contemplated that an end portion of the elongate shaft portion 26 can be configured for engagement with an abutment and/or prosthesis as described herein such that the elongate shaft portion can effectively act as an attachment element as described herein.

Figure 7A:
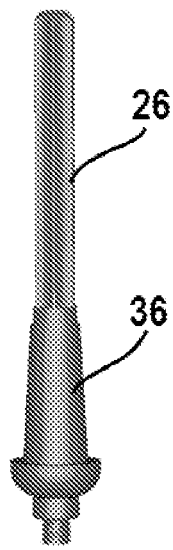
FIGS. 7A-7C depict exemplary stems as described herein.
Figure 7B:
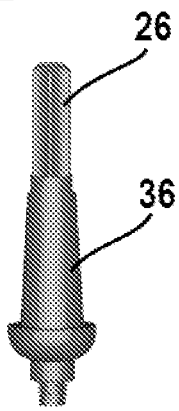
Figure 7C:
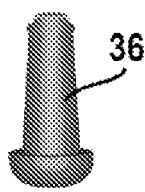

Optionally, in one aspect, and as shown in FIG. 7C, the stem 20 can comprise a collar portion 36 with no elongate shaft portion 26. In this aspect, the elongate portion 39 of the collar portion 36 can be configured for secure receipt within the prepared site of the selected bone.

In use, the disclosed implant system can be used in a method of securing a prosthesis thereto a selected bone of a limb of a subject. In one aspect, the method of securing the prosthesis can comprise preparing a selected bone for receipt of the implant. In this aspect, it is contemplated that the step of preparing the selected bone can comprise preparing a medullary cavity of the selected bone for receipt of the implant. In another aspect, the method of securing the prosthesis can comprise positioning the stem within the prepared site of the selected bone. Optionally, when the stem comprises a collar portion that is selectively detachable from the elongate shaft portion of the stem, the method of securing the prosthesis can further comprise securing a portion of the elongate shaft portion of the stem within the cavity of the collar portion. In an additional aspect, the method of securing the prosthesis can optionally comprise securing the abutment to the implant such that the longitudinal axis of the abutment is substantially axially aligned with the longitudinal axis of the stem. In a further aspect, the method of securing the prosthesis can comprise attaching the prosthesis to at least a portion of the abutment.

Upon secure receipt of the stem within the prepared site such that the longitudinal axis of the stem is substantially axially aligned with the longitudinal axis of the selected bone, the stem can be configured to promote integration of the selected bone of the subject and the skin of the subject into the stem. More particularly, it is contemplated that the porous material coating of the stem can promote integration of bone and skin of the subject into the stem such that a seal is formed between the skin of the subject and the implant. It is further contemplated that the seal that is formed between the skin of the subject and the stem can reduce the likelihood of infection in the subject and minimize the possibility of formation of a pocket between the skin of the subject and the stem.

Although the exemplary stems and abutments are described herein as being configured for operative securement to one another, it is contemplated that the stems described herein can be configured for operative securement to other conventional abutment designs. It is further contemplated that the abutments described herein can be configured for operative securement to other conventional stem designs.

It is contemplated that one or more of the individual components of the implant system described herein can be provided in the form of a kit. It is further contemplated that the respective components of the implant system described herein can comprise labelling, color-coding, or other indicia of the particular sizing and/or attachment features of the component that enable a surgeon or other medical practitioner to determine whether the component is appropriate use in a particular procedure and/or whether the component is complementary in size and/or function to other components of an implant system.

EXPERIMENTAL EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

The metacarpal III bones from 20 mature crossbred sheep carcasses were imaged by using a clinically based CT scanner (LightSpeed VCT XT, GE Healthcare, Milwaukee, Wis.) at a tube voltage of 100 kVp with an automatically calibrated variable milliampere current and stored digitally as DICOM files. These images were reconstructed using commercially available software (MIMICS, Materialise Corp., Plymouth, Mich.), then ported to a custom analysis program for analyses (MatLab, MathWorks Corp., Natick, Mass.) to provide AP and ML dimensions of the medullary canal at 1 mm increments throughout the length of each bone. From these data, three implant sizes and surgical broaches, corresponding to the 25th, 50th, and 75th percentiles were designed (Intelligent Implant Systems, LLC, Charlotte, N.C.) and fabricated (IMDS Co-Innovative, Logan, Utah) from medical grade Ti-6Al-4V alloy.

Both the control and experimental groups were geometrically similar. The intramedullary portion was textured by grit blasting to facilitate immediate bone attachment and to achieve bone-implant integration. Both implants had central ribs to improve initial fixation. For the control group, the Ti subdermal surface was polished smooth [surface roughness (Ra)=1.7±0.1 μm] mimicking human implant designs. For the experimental group, the subdermal barrier structure was coated with pure Ti porous coating, $P^2$ type [porosity=52±12% and surface roughness (Ra)=113±25 μm; Thortex Corp., Portland, Oreg.]. Both groups had a porous-coated structure at the base of the endo-prosthetic portion to promote skeletal attachment. The coating was made with the same $P^2$ type coating. All implants were passivated and sterilized using ASTM standard B 600-91.

Initially, 23 skeletally mature 2- to 3-year-old mixed breed sheep were divided into two groups using a random number generator: G1—Experimental group (n=14, porous-coated implants) and G2—Control group (n=9, smooth implants). Each sheep underwent a single-stage "amputation and implantation surgery." All work was performed in accordance with an institutionally approved IACUC protocol at an AAALAC-approved animal care facility (IMDS Discovery Research, Logan, Utah).

Preoperative radiographs were taken at a standard distance from the limb with a 3D reference object for size calibration. Templates were used to determine the best fit implant size. After induction of general anesthesia [diazepam (0.1-0.5 mg/kg) and ketamine hydrochloride (4.4-7.5 mg/kg)], sheep were maintained under inhalant anesthesia (0.5-5% isoflurane in oxygen), the right forelimb was shaved, scrubbed with Betadine soap, prepped with Betadine and alcohol, and then draped with sterile drapes. A temporary rubber glove tourniquet was applied proximal to the carpal-metacarpal joint while the skin incision was made, and hemostasis was obtained with electrocautery. A transverse anterior incision was then made immediately above the hoof, and dissection was carried proximally, both medially and laterally, in the coronal midline of the limb to above the dewclaws. A connecting posterior transverse incision allowed the final amputation to exclude the dewclaws. Careful dissection established an anteriorly based skin flap, devoid of subcutaneous fat and with an intact blood supply. The skin flap was protected in a saline moistened gauze sponge. The flexor and extensor tendons were tenodesed, in neutral joint position, within the tendon sheaths, using #0 FiberWire and then transected distally. The metacarpal-phalangeal joint was disarticulated, and the metacarpal was transected with a bone saw immediately above the junction between the condyles and the metaphyseal flare.

The distal transverse cancellous bone surface was drilled axially into the canal, and the canal was reamed and broached to accept the implant. Saline irrigations were used to minimize over-heating. Each G1 sheep was surgically implanted with a porous-coated subdermal barrier-incorporated percutaneous OI device; each G2 sheep was implanted with a similar device but with a smooth subdermal barrier OI implant. A hand mallet was used to impact the device into the canal. The skin flap was then revised, and a sagittal stab wound was made in the center of the flap slightly smaller than the Morse taper and porous collar of the implant. The skin was then stretched around the taper and the porous collar, establishing an immediate tight attachment and seal. A subcutaneous closure was done with interrupted 3-0 Biosyn sutures, and the skin was closed with a running 2-0 Biosyn subcuticular suture. The surgical site was dressed with Silvasorbl hydrogel, and a moderately compressive wrap was maintained for 2 weeks. The exo-prosthetic "hoof" was secured to the Morse taper of the OI implant.

Naxcel (1.1 mg/kg 1V) was given intra-operatively for antibiotic prophylaxis followed by a 7-day antibiotic course of Excede® (6.6 mg/kg). Ketoprofen (4.4 mg/kg), and Fentanyl patches (100 µg/h) were used for 5-7 days to control pain. The skin-implant interface was debrided weekly with PureWorks® (benzethonium chloride) antiseptic spray by training the sheep to sit. While held, the stoma on the right forelimb was gently mechanically debrided with a 4×4 sponge soaked with PureWorks®. After wiping away any loose debris, a final spray was made directly on the skin-implant interface. Radiographs were obtained at 3-month intervals to assess bone-implant integration and to check for early loosening and possible osteomyelitis.

Sheep were excluded if clinical or radiological signs of fracture occurred during surgery or the postoperitive period. Sheep were euthanized early if they exhibited clinical signs of infection and the infection site was assessed to be Grade 3 on the Checketts scale. (Grade 1=slight redness around the pin site with slight swelling; Grade 2=swelling, clear discharge, and tenderness around the implant exit site; Grade 3=Grade 2+infection with purulent discharge and non-weight bearing in the amputated right limb.

At necropsy, culture swabs were collected from: a site distal to the implant to characterize normal skin flora; at the skin-implant interface; and the bone marrow of the proximal medullary canal to examine for periprosthetic and deep bone infection.

At necropsy, the right (implanted) and left (un-implanted) forelimbs were harvested, processed, and subjected to histological analysis. At least two coronal slices were prepared from each specimen of the skin-implant interface. These were ground to ~50 mm sections, stained with hematoxylin and eosin or Sanderson's rapid bone stain, and examined for signs of inflammatory cells, viable epithelial cells, and dermal and epithelial tissue integration.

The criteria for infection were: (i) clinical signs of infection, (ii) positive culture results for tissue and/or marrow samples, or (iii) histological evidence. Animals were deemed infected, if 2 of 3 criteria were met. Statistical analysis between the groups was performed using a pre-specified survival analysis approach to allow for unequal follow-up times, using the log-rank test and reported descriptively using a Kaplan-Meier survival probability graph. Statistics were computed using Stata version 11 statistical software (StataCorp LP, College Station, Tex.). Given the small sample size, an "exact" version of the log-rank test was also computed using the StatXact version 8 software (Cytel, Inc., Cambridge, Mass.). The p-value only changed from p=0.018 to p=0.017, so the ordinary log-rank test is reported. A two-sided comparison was used, with $p<0.05$ indicating significance.

The disparity in the animal number between groups was due to the fact that the data presented here were part of a larger study of 86 sheep. In that study, 77 sheep were implanted with a porous-coated implant and nine were implanted with a smooth percutaneous OI prosthesis. Sheep from the porous-coated group were sacrificed at 0-, 3-, 6-, 9-, and 12-month time points to investigate progress of bone and skin integration, where half of the sheep from the porous implant group (n=~7/time point) were subjected to biomechanical testing and the rest (n=~7/time point) were included in histological analyses. These results will be published elsewhere. Both porous and smooth groups from the larger study had 20% extra animals included, in case of complications leading to exclusion. In the current study, a postoperative spiral fracture occurred in one G2 animal. This left 8 sheep in G2. Histology, however, was performed on 7 G1 and 8 G2 animals.

Following surgery and recovery from anesthesia, sheep could ambulate within an hour with minimal limping. The limp disappeared over the first week after surgery. Force plate analysis was performed on the 12-month sheep in the larger study; these data showed that sheep were loading the implanted limb up to 80% of the pre-amputated load by 1 month.

Figure 8:
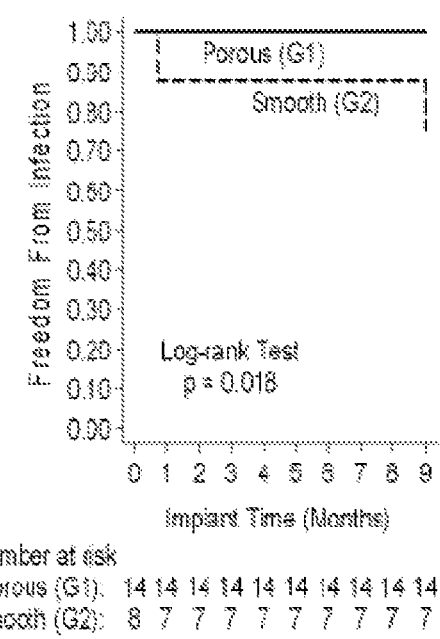
FIG. 8 depicts a Kaplan-Meier survival curve of smooth (n=8) and porous-coated (n=14) groups as described in the Experimental Examples section, which follows. The Logrank test showed a significant difference (p=0.018) between groups, indicating that the porous-coated subdermal barrier as described herein prevents infection when compared to a smooth subdermal barrier.

One G2 animal was euthanized at 23 days because of infection (Grade 3); a second animal exhibited superficial infection with severe fluid drainage (Grade 2), but survived to the study end point (Table 1). Skin tissue samples showed bacterial growth and histopathological evidence of infection. Two G1 sheep had serous discharge but no clinical signs of infection at euthanasia. Accounting for time to infection, significantly greater infection occurred in G2 animals (logrank test, p=0.018, FIG. 8).

TABLE 1

|  | Porous-coated group (G1) | Smooth group (G2) |
|---|---|---|
| Total number of surgeries | 14 | 9 |
| Term euthanasia | 14 | 7 |
| Euthanized due to fractured bone | 0 | 1 |
| Infection | — | 2 |

Although all skin-implant interfaces (100%) were colonized with normal skin flora and/or environmental organisms, none of the bone marrow specimens produced positive growth for potential pathogenic microbial cultures (Table 2). However, 2 skin punch samples collected at necropsy from the G2-infected animals produced positive results for coagulase negative *Staphylococcus*, *Enterobacter*, and *Bacilli* organisms. Both animals were confirmed to be infected by clinical and histopathological findings. The skin-implant interface exhibited a breached epithelial seal with increased infiltration of inflammatory cells in the tissues of the periprosthetic region. All skin-implant interfaces from the smooth-group were hyper-cellular with a large population of fibroblasts and some lymphocytes, indicating an ongoing tissue repair process, possibly associated with low-grade infections. Although an immuno-histochemical assay would have verified the interpretation, it was impossible to do so on PMMA embedded samples.

TABLE 2

| Sampling site | Porous-coated implant group (G1) | Smooth implant group (G2) |
| --- | --- | --- |
| Skin-implant interface | | |
| Colonized | 14 | 8 |
| Infected | 0 | 2 |
| Periprosthetic skin tissue | 0 | 2 |
| Bone marrow | 0 | 0 |
| Blood | 0 | 0 |

Although most G2 animals (6/8, 75%) survived without infection, higher degrees of proximal skin migration occurred when compared to the G1 group with a difference in marsupialization of the skin between the groups. The rate of migration was 0.6±0.1 mm/month for the G1 group and 2.1±0.3 mm/month for G2 group.

It should be appreciated that the angles and dimensions depicted in the Figures may be exaggerated for clarity and, consequently, may not be to scale.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. An implant system for securing a prosthesis to a prepared site within a selected bone of a tissue region of a subject, the implant system comprising:

a stem having a longitudinal length from a first end of the stem to the second end of the stem along a longitudinal axis, the stem comprising:

an elongate shaft portion having an outer surface and defining an insertional end of the stem, the insertional end of the stem configured for receipt within the prepared site, the outer surface including at least one porous region comprising a plurality of porous sections spaced about a circumference of the outer surface, a plurality of regions extending continuously through the porous region along the longitudinal axis of the stem and separating adjacent porous sections of the plurality of porous sections, and one or more non-porous regions, wherein the at least one porous region has a total porous region length of a portion of the longitudinal length of the stem, and wherein the non-porous regions have a total non-porous region length of a remainder of the longitudinal length of the stem; and a collar portion defining the second end of the stem, the second end of the stem being spaced from the insertional end of the stem along the longitudinal axis of the stem, the collar portion defining a shoulder surface extending radially outwardly from the outer surface of the elongate shaft portion, wherein the collar portion and the elongate shaft portion cooperate to define a central bore extending along at least a portion of the longitudinal length of the stem, and wherein the ratio between the longitudinal length of the stem and the total porous region length of the at least one porous region ranges from about 3:1 to about 10:1; and an abutment having a longitudinal axis, an attachment element, and a post having an outer surface and being operatively coupled to the attachment element, the attachment element of the abutment being configured for complementary receipt within the central bore of the stem such that the longitudinal axis of the abutment is substantially aligned with the longitudinal axis of the stem, at least a portion of the post being configured for selective secure attachment to the prosthesis, wherein, upon secure receipt of the stem within the prepared site, the at least one porous region of the stem are configured to promote integration of the selected bone of the subject into the stem and the shoulder surface is configured to abut the selected bone, and wherein at least a portion of the outer surface of the post of the abutment is configured to inhibit bio-adhesion.

2. The implant system of claim 1, wherein the at least one porous region of the elongate shaft portion of the stem comprise porous titanium.

3. The implant system of claim 1, wherein the shoulder surface of the collar portion of the stem comprises a porous region configured to promote integration of the selected bone of the subject into the stem.

4. The implant system of claim 3, wherein the porous region of the shoulder surface of the collar portion of the stem comprises porous titanium.

5. The implant system of claim 1, wherein the collar portion of the stem comprises an outer surface, and wherein at least a portion of the outer surface of the collar portion is configured to inhibit bio-adhesion.

6. The implant system of claim 1, wherein the at least one porous region of the elongate shaft portion of the stem is recessed relative to the outer surface of the non-porous regions of the elongate shaft portion.

7. The implant system of claim 1, wherein the portion of the outer surface of the post of the abutment that is configured to inhibit bio-adhesion comprises an ultra-low friction surface.

8. The implant system of claim 1, wherein the portion of the outer surface of the post of the abutment that is configured to inhibit bio-adhesion comprises a highly polished surface.

9. The implant system of claim 1, wherein the post of the abutment has an insertional first end portion, an opposed second end portion, and a central portion positioned therebetween the first end portion and the second end portion along the longitudinal axis of the abutment, wherein the post is operatively coupled to the attachment element such that, upon complementary receipt of the attachment element within the implant stem, the insertional first end portion of the post is configured to be operatively positioned relative to the stem, and wherein the opposed second end portion of the post is configured for selective secure attachment to the prosthesis.

10. The implant system of claim 9, wherein the central portion of the post of the abutment is configured to inhibit bio-adhesion.

11. The implant system of claim 1, wherein the abutment further comprises a fixation element secured to the outer surface of the post at a selected position along the longitudinal axis of the abutment such that the fixation element extends radially outwardly relative to the outer surface of adjoining portions of the post, thereby defining a fixation surface configured to abut soft tissue of the subject proximate the prepared site.

* * * * *

UNITED STATES PATENT AND TRADEMARK OFFICE
CERTIFICATE OF CORRECTION

| | | |
|---|---|---|
| PATENT NO. | : 9,668,889 B2 | Page 1 of 1 |
| APPLICATION NO. | : 14/123719 | |
| DATED | : June 6, 2017 | |
| INVENTOR(S) | : Brian Mueller Holt et al. | |

It is certified that error appears in the above-identified patent and that said Letters Patent is hereby corrected as shown below:

In Column 1, Lines 16-28, please delete:
"This invention was made with United States government support under Grant PR054520 awarded by the Department of Defense, Grant R01HD061014 awarded by the National Institutes of Health, Grant IRCI AR058356 awarded by the National Institutes of Health, Grant #RX000262-01 awarded by the Department of Veterans Affairs, Grant #A5-4159RA awarded by the Department of Veterans Affairs, Grant #10091004 awarded by the U.S. Army Medical Research Materiel Command, and Grant #W81XWH-05-I-0628 awarded by the Telemedicine and Advanced Technology Research Center of the U.S. Army's Military Amputee Research Program. The government has certain rights in this invention."

And replace with the following paragraph:
--This invention was made with government support under Grant Numbers HD061014 and AR058356 awarded by the National Institutes of Health and Grant Numbers W81XWH-06-1-0574 and W81XWH-05-1-0628 awarded by the Army/MRMC. The government has certain rights in the invention.--

Signed and Sealed this
Tenth Day of April, 2018

Andrei Iancu
*Director of the United States Patent and Trademark Office*

UNITED STATES PATENT AND TRADEMARK OFFICE
CERTIFICATE OF CORRECTION

PATENT NO. : 9,668,889 B2  
APPLICATION NO. : 14/123719  
DATED : June 6, 2017  
INVENTOR(S) : Brian Mueller Holt et al.

Page 1 of 1

It is certified that error appears in the above-identified patent and that said Letters Patent is hereby corrected as shown below:

In the Specification

In Column 1, Line 16 delete:
"This invention was made with government support under Grant Numbers HD061014 and AR058356 awarded by the National Institutes of Health and Grant Numbers W81XWH-06-1-0574 and W81XWH-05-1-0628 awarded by the Army/MRMC. The government has certain rights in the invention."

And replace with:
--This invention was made with government support under grant numbers HD061014 and AR058356 awarded by the National Institutes of Health and grant numbers W81XWH-06-1-0574, W81XWH-05-1-0628, and W81XWH-11-1-0435 awarded by the Army/MRMC. The government has certain rights in the invention.--

This certificate supersedes the Certificate of Correction issued April 10, 2018.

Signed and Sealed this  
Seventeenth Day of March, 2020

Andrei Iancu  
*Director of the United States Patent and Trademark Office*